US012721846B2

(12) United States Patent
Nirogi et al.

(10) Patent No.: US 12,721,846 B2
(45) **Date of Patent: *Sep. 1, 2026**

(54) METHODS FOR TREATING BEHAVIORAL AND PSYCHOLOGICAL SYMPTOMS IN PATIENTS WITH DEMENTIA

(71) Applicant: SUVEN LIFE SCIENCES LIMITED, Hyderabad-Telangana (IN)

(72) Inventors: Ramakrishna Nirogi, Hyderabad-Telangana (IN); Anil Karbhari Shinde, Hyderabad-Telangana (IN); Veena Reballi, Hyderabad (IN); Pradeep Jayarajan, Hyderabad (IN); Renny Abraham, Hyderabad (IN); Venkateswarlu Jasti, Hyderabad (IN); Rajesh Badange, Hyderabad (IN); Vijay Sidram Benade, Hyderabad (IN)

(73) Assignee: SUVEN LIFE SCIENCES LIMITED, Hyderabad-Telangana (IN)

( * ) Notice: Subject to any disclaimer, the term of this patent is extended or adjusted under 35 U.S.C. 154(b) by 965 days.

This patent is subject to a terminal disclaimer.

(21) Appl. No.: 17/780,456

(22) PCT Filed: Dec. 2, 2020

(86) PCT No.: PCT/IB2020/061367
§ 371 (c)(1),
(2) Date: May 26, 2022

(87) PCT Pub. No.: WO2021/111320
PCT Pub. Date: Jun. 10, 2021

(65) Prior Publication Data

US 2023/0000859 A1 Jan. 5, 2023

(30) Foreign Application Priority Data

Dec. 2, 2019 (IN) ............................ 201941049513
Dec. 2, 2019 (IN) ............................ 201941049515

(51) Int. Cl.

| | |
|---|---|
| *A61K 31/496* | (2006.01) |
| *A61K 31/13* | (2006.01) |
| *A61K 31/445* | (2006.01) |
| *A61P 25/28* | (2006.01) |

(52) U.S. Cl.
CPC ............ *A61K 31/496* (2013.01); *A61K 31/13* (2013.01); *A61K 31/445* (2013.01); *A61P 25/28* (2018.01)

(58) Field of Classification Search
CPC .................................................... A61K 31/496
See application file for complete search history.

(56) References Cited

U.S. PATENT DOCUMENTS

| | | | |
|---|---|---|---|
| 2019/0125743 | A1 | 5/2019 | Nirogi et al. |
| 2019/0160055 | A1 | 5/2019 | Nirogi |
| 2022/0409614 | A1 | 12/2022 | Nirogi |

FOREIGN PATENT DOCUMENTS

| | | | | |
|---|---|---|---|---|
| JP | T-2007-526335 | | 9/2007 | |
| WO | 2005/084655 | A1 | 9/2005 | |
| WO | WO-2012173808 | A1 * | 12/2012 | ............. A61P 25/24 |
| WO | 2015083179 | A1 | 6/2015 | |
| WO | 2017194496 | A1 | 11/2017 | |
| WO | 2017199070 | A1 | 11/2017 | |
| WO | 2017199071 | A1 | 11/2017 | |
| WO | 2017199072 | A1 | 11/2017 | |
| WO | 2019008484 | A1 | 1/2019 | |

OTHER PUBLICATIONS

Kuan et al., "Cell type-specific gene expression patterns associated with posttraumatic stress disorder in World Trade Center responders" Transl. Psychiatry 2019, 9(1), 123 (11 pages).
Malpas, "The histopathological staging of tau, but not amyloid, corresponds to antemortem cognitive status, dementia stage, functional abilities, and neuropsychiatric symptoms" Int. J. Neurosci. 2021, 131(8), 800 (17 pages).
Banning et al., "The Association Between Biomarkers and Neuropsychiatric Symptoms Across the Alzheimer's Disease Spectrum" Am. J. Geriatr. Psychiatry 2020 (Article in Press, 28(7), 735, 10 pages, doi.org/10.1016/j.jagp.2020.01.012).
Garre-Olmo et al., "Grouping and Trajectories of Neuropsychiatric Symptoms in Patients with Alzheimer's Disease. Part II: Two-Year Patient Trajectories" J. Alzheimer's Dis. 2010, 22(4), 1169 (with Abstract).
Eikelboom et al., "Neuropsychiatric and Cognitive Symptoms Across the Alzheimer Disease Clinical Spectrum" Neurology 2021, 97(13), e1276-e1287 (12 pages).
Wise et al., "Time course of neuropsychiatric symptoms and cognitive diagnosis in National Alzheimer's Coordinating Centers volunteers", Alzheimer's Dement. (Amst.) 11:333-339 (2019).
Devanand, "Associations Between Neuropsychiatric Symptoms and Neuropathological Diagnoses of Alzheimer Disease and Related Dementias" JAMA Psychiatry 2022, 79(4), 359-367 (provided over 19 pages).

(Continued)

*Primary Examiner* — Yong S. Chong
(74) *Attorney, Agent, or Firm* — IPHORGAN LTD.

(57) ABSTRACT

The present invention provides a method for treating behavioral and psychological symptoms in patients with dementia comprising administering an effective dose of pure 5-$HT_6$ receptor antagonist and acetylcholinesterase inhibitor or NMDA receptor antagonist. The present invention also relates to a pharmaceutical combination comprising pure 5-$HT_6$ receptor antagonist and acetylcholinesterase inhibitor or NMDA receptor antagonist, in particular for treating behavioral and psychological symptoms in patients with dementia. The present invention further provides use of the said compounds in the manufacture of a medicament, and a pharmaceutical composition comprising the said compounds intended for the treatment of disorders described herein.

17 Claims, 3 Drawing Sheets

(56) References Cited

OTHER PUBLICATIONS

Nirogi et al., "Effect of masupirdine (SUVN-502) on cognition in patients with moderate Alzheimer's disease: a randomized, double-blind, phase 2, proof-of-concept study" Alzheimer's Dement. 2022, 8, e12307 (12 pages).
Elder et al., "Sleep disturbances in Lewy body dementia: a systematic review" Int. J. Geriatr. Psychiatr. 2022, 37 (10), 1-22.
Cummings, "Lessons Learned from Alzheimer Disease: Clinical Trials with Negative Outcomes" Clin Transl Sci (2018) 11, 147-152.
Atri et al., "Effect of Idalopirdine as Adjunct to Cholinesterase Inhibitors on Change in Cognition in Patients with Alzheimer Disease Three Randomized Clinical Trials" JAMA 2018, 319(2), 130-142.
Lang et al., "Intepirdine as adjunctive therapy to donepezil for mild-to-moderate Alzheimer's disease: a randomized, placebo-controlled, phase 3 clinical trial (MINDSET)" Alzheimer's Dement. 2021;7:e12136 (9 pages).
Fullerton et al., "A Phase 2 clinical trial of PF-05212377 (SAM-760) in subjects with mild to moderate Alzheimer's disease with existing neuropsychiatric symptoms on a stable daily dose of donepezil" Alzheimer's Res. Ther. (2018) 10:38 (10 pages).
Jones, "Dimebon disappointment" Alzheimer's Res. Ther. 2010, 2:25 (3 pages).
Nirogi et al., "Progress in Investigational Agents Targeting Serotonin-6 Receptors for the Treatment of Brain Disorders" Biomol. 2023, 13, 309 (19 pages).
Jayarajan, Pradeep et al., "P1-302: 5-HT6 Antagonist SUVN-502 potentiates the procognitive and neurochemical effects of donepezil and memantine", Alzheimer's & Dementia: the Journal of the Alzheimer's Association, vol. 11, No. 7S_Part_10, Jul. 1, 2015, p. 472, USA.
Jayarajan, Pradeep et al., "P1-089: SUVN-502 + Donepezil + Memantine (Triple Combination): First- in-Class and a Promising New Approach for the Symptomatic Treatment of Alzheimer's Disease Dementia", Alzheimer's & Dementia: the Journal of the Alzheimer's Association, vol. 15, No. 7, Jul. 1, 2019, Elsevier, New York, NY, USA.
Nirogi Ramakrishna et al., "P4-660: Triple Therapy with Masupirdine (SUVN-502), a 5-HT6 Antagonist, Doneprezil and Memantine in Moderate Alzheimer's Disease: Baseline Patient Characteristics in a Phase-2A Study", Alzheimer's & Dementia: the Journal of the Alzheimer's Association, vol. 15, No. 7, Jul. 1, 2019, Elsevier, New York, NY, USA.
Devshi, Rajal et.al.; "Prevalence of Behavioural and Psychological Symptoms of Dementia in Individuals with Learning Disabilities"; Diagnostics (Basel). Dec. 2015; 5(4): 564-576.
Atri, Alireza et. al., "Triple therapy with Suvn-502, 5-Ht6 antagonist, donepezil and memantine in moderate Alzheimer's disease: Baseline characteristics in Phase-2a study" Journal of prevention of Alzheimer's disease, vol. 5, No. 1, Oct. 4, 2018.
Ennaceur, A., "One-trial object recognition in rats and mice: Methodological and theoretical issues", Behavioural Brain Research, 2010, 244-254, Elsevier B.V.
Vorhees, Charles, WILIAMS, Michael, "Morris water maze: procedures for assessing spatial and related forms of learning and memory", Nature Protocols, 2006, vol. 1 No. 2, Nature Publishing Group.
Parsons, Chris G. et al., "Memantine and Cholinesterase Inhibitors: Complementary Mechanisms in the Treatment of Alzheimer's Disease", Neurotox Res. Journal, 2013, 24:358-369.
Wicke, Karsten et. al., "Investigational drugs targeting 5-HT6 receptors for the treatment of Alzheimer's disease", Expert Opinion on Investigational Drugs, 2015, 1515-1528.
Jellinger, Kurt A., "Cerebral correlates of psychotic syndromes in neurodegenerative diseases", Journal of Cellular and Molecular Medicine, 2012, 995-1012, vol. 16 No. 5, Blackwell Publishing Ltd.
Schneider, Lon S. et al., "Effectiveness of Atypical Antipsychotic Drugs in Patients with Alzheimer's Disease", The New England Journal of Medicine, Oct. 12, 2006, 1525-1538, vol. 355 No. 15.
Ballard, Clive et. al., "Evaluation of the safety, tolerability, and efficacy of pimavanserin versus placebo in patients with Alzheimer's disease psychosis: a phase 2, randomised, placebo-controlled, double-blind study", The Lancet—Neurology, Mar. 2018, vol. 17, 213-222.
Porsteinsson, Anton P. et al., "Effect of Citalopram on Agitation in Alzheimer Disease: the CitAD Randomized Clinical Trial", The Journal of the American Medical Association, 2014, 682-691, vol. 311 No. 7.
Waldermar, Gunhild et. al., "Effect of donepezil on emergence of apathy in mild to moderate Alzheimer's disease", International Journal of Geriatric Psychiatry, 2011, vol. 26, 150-157, John Wiley & Sons, Ltd.
Howard, Robert J. et al., "Donepezil for the Treatment of Agitation in Alzheimer's Disease", The New England Journal of Medicine, Oct. 4, 2007, 1382-1392, vol. 357 No. 14.
PCT, International Preliminary Report on Patentability dated Feb. 25, 2022.
PCT, International Search Report dated Mar. 17, 2021.
PCT, Written Opinion of the International Searching Authority dated Mar. 17, 2021.
PCT, Written Opinion of the International Preliminary Examining Authority dated Aug. 19, 2021.
Alzheimer's Association, "Medications for Memory" https://www.alz.org/alzheimers-dementia/treatments/medications-for-memory (Jan. 30, 2019) (7 pages), as archived by The Wayback Machine https://web.archive.org/web/20190130194937/https://www.alz.org/alzheimers-dementia/treatments/medications-for-memory.
International Psychogeriatric Association, "The IPA Complete Guide to Behavioral and Psychological Symptoms of Dementia" www.ipa-online.org (2015) (251 pages).
American Psychiatric Association, "Diagnostic and Statistical Manual of Mental Disorders, Fifth Ed. (DSM-5)", American Psychiatric Publishing, Arlington VA, USA (2013), pp. 591-644.
Alzheimer's Association, "Medications for Memory, Cognition, and Dementia—Related Behaviors" https://www.alz.org/alzheimersdementia/treatments/medications-for-memory (2025) (21 pages).
Ohno et al., "Antipsychotic Treatment of Behavioral and Psychological Symptoms of Dementia (BPSD): Management of Extrapyramidal Side Effects" Frontiers in Pharmacology (10) Article 1045, 10 pages (2019).
Jack et al., "NIA-AA Reserch Framework: Toward a biological definition of Alzheimer's disease" Alz. Dement. Apr. 14, 2018(4):535-562 (doi:10.1016/j.jalz.2018.02.018 (54 pages).
Hoglinger et al., "A biological classification of Parkinson's disease: the SynNeurGe research diagnostic criteria" Lancet Neurol. 2024 23:191-204.
Forester and Oxman, "Measures to Assess the Noncognitive Symptoms of Dementia in the Primary Care Setting" J.Clin.Psychiatry 2003 5:158-163.
Ennaceur and Delacour, "A new one-trial test for neurobiological studies of memory in rats. 1: Behavioral data" Behav. Brain Res. 1988 31:47-59.
Cerejeira et al., "Behavioral and psychological symptoms of dementia" Frontiers in Neurology 2012 3(73):1-21.
Garre-Olmo et al., "Grouping and Trajectories of Neuropsychiatric Symptoms in Patients with Alzheimer's Disease. Part II: Two-Year Patient Trajectories" 2010 22:1169-1180.
Pfizer Press Release, "Pfizer and Medivation Announce Results From Two Phase 3 Studies in Dimebon (latrepirdine*) Alzheimer's Disease Clinical Development Program" Pfizer.com (Mar. 2, 2010) https://www.pfizer.com/news/press-release/press-release-detail/pfizer_and_medivation_announce_results_from_two_phase_3_studies_in_dimebon_latrepirdine_alzheimer_s_disease_clinical_development_program (8 pages).
Fernandez, "SYN120 (a dual 5-HT6/5-HT2A antagonist) study to evaluate safety, tolerability, and efficacy in Parkinson's disease dementia (SYNAPSE): Phase 2a study results (S4.005)" Neurology (2019) vol. 92 (15_supplement S4.005).

(56) References Cited

OTHER PUBLICATIONS

Zakaib, "Intepirdine Joins the Ranks of Failed Alzheimer's Drugs" (2017) Alzforum.com, HTTPS://WWW.ALZFORUM.ORG/news/research-news/intepirdine-joins-ranks-failed-alzheimers-drugs (4 pages).
Clinicaltrials.gov, "Study Comparing 3 Dosage Levels of SAM-531 in Outpatients With Mild to Moderate Alzheimer Disease" ClinicalTrials.gov(2013), https://clinicaltrials.gov/ct2/show/NCT00895895 (24 pages).
Atri et al., Memantine Added to Background Cholinesterase Inhibitors Reduces Agitation in Alzheimer's Disease (P6.175), Neurology 2018, 90(15_Supplement) (2 pages).
Paterson et al., Cerebrospinal Fluid in the Differential Diagnosis of Alzheimer's Disease. Clinical Utility of an Extended Panel of Biomarkers in a Specialist Cognitive Clinic. Alzheimer's Research & Therapy 2018. 10(1) (11 pages).
Grandhi Venkata Ramalingayya et al., "SUVN-502: A pure 5-HT6 receptor antagonist ameliorates senile dementia in animal models" Alzheimer's & Dementia: the Jornal of Alzheimer's association, Elseiver, NY, Newyork, US, vol. 15, No. 7, Jul. 1, 2019 (See D1).
Cummings J, Nirogi R., Jayarajan P, Shinde A, Jasti V: "P038: potential benefits of Masupirdine (Suvn-502) on behavioral and psychological symptoms in patients with moderate Alzheimer's disease". Journal of prevention ofAlzheimer's disease, vol. 6, No. 1, Dec. 8, 2019, p. S68 (see D9).
Alzheimer's dement. 2019, 15(7Suppl) P604 (Abstract P2-083): "P2-083: Suvn-502: a pure 5-ht6 receptor antagonist ameliorates senile dementia in animal models" (See D1).
Alzheimer's dement. 2015, 11 (7Suppl.) P472 (Abstract P1-302) "P1-302: 5-ht6 antagonist SUVN-502 potentiates the procognitive and neurochemical effects of donepezil and memantine" (See 5).
Alzheimer's Dement. 2019, 15(7Suppl.), P269 (Abstract P1-089): "P1-089: Suvn-502 + donepezil + memantine (triple combination): first-in-class and a promising new approach for the symptomatic treatment of Alzheimer's disease dementia" (See D6).
Alzheimer's Dement 2019. 15(7Suppl.), P1584 (Abstract P4-660): "P4-660: Triple therapy with masupirdine (suvn-502), a 5-ht6 antagonist, donepezil and memantine in moderate Alzheimer's disease: baseline patient characteristics in a phase-2a study" (See D7).
P. Jayarajan et al., Potential Benefits of Masupirdine (SUVN-502) on Behavioral and Psychological Symptoms in Patients With Moderate Alzheimer's Disease. The Journal of Prevention of Alzheimer's Disease, 2019, p. S68, Abstract P038, vol. 6, Supplement No. 1 (See D9).
Clive G. Ballard et al., Management of agitation and aggression associated with Alzheimer disease, Nature Reviews, Neurology, May 2009, pp. 245-255, vol. 5, No. 5, Macmillan Publishers Limited.
U.S. Patent and Trademark Office, Office Actions issued in U.S. Appl. No. 17/780,734 on Mar. 20, 2025, Jul. 14, 2025, Jan. 9, 2026, Mar. 17, 2026, and Examiner Interview Summary issued Apr. 20, 2026.
European Patent Office, "International Search Report" and Written Opinion issued Mar. 17, 2021 in counterpart PCT Application No. PCT/IB2020/061367.
European Patent Office, "International Search Report" and Written Opinion issued in PCT Application No. PCT/IB2020/061383.

* cited by examiner

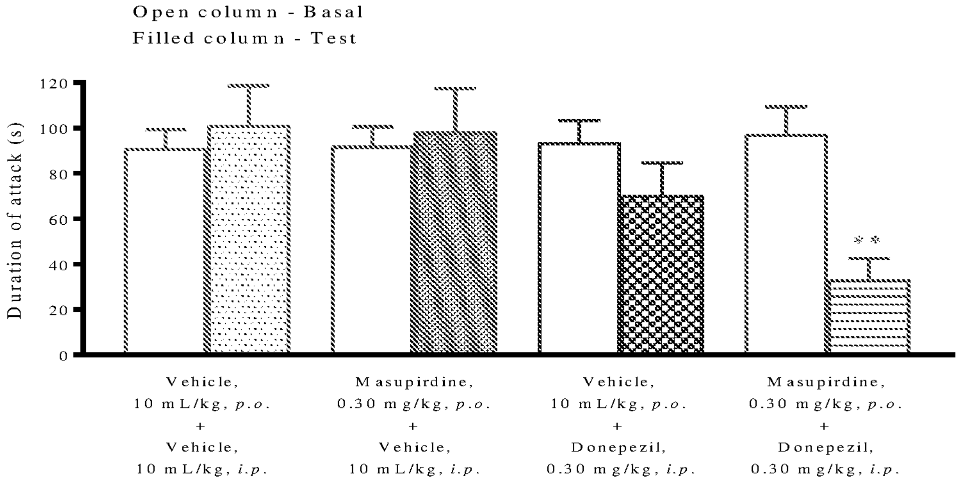

Data represents Mean± SEM of duration of attack, Student's paired *t*-test, **p<0.01 Vs Basal, n=9

Figure 1: Effect of combined masupirdine and donepezil on aggression levels compared to masupirdine or donepezil alone.

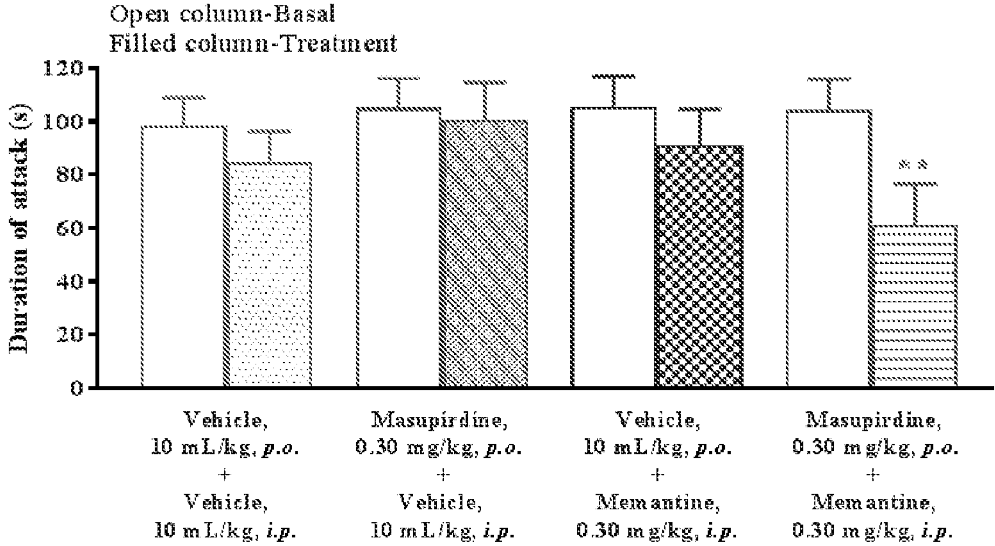

Data represents mean ± SEM of duration of attack, Student's paired t-test, **p<0.01 vs basal, n=9-10.

Figure 2: Effect of combined masupirdine and memantine on aggression levels compared to masupirdine or memantine alone.

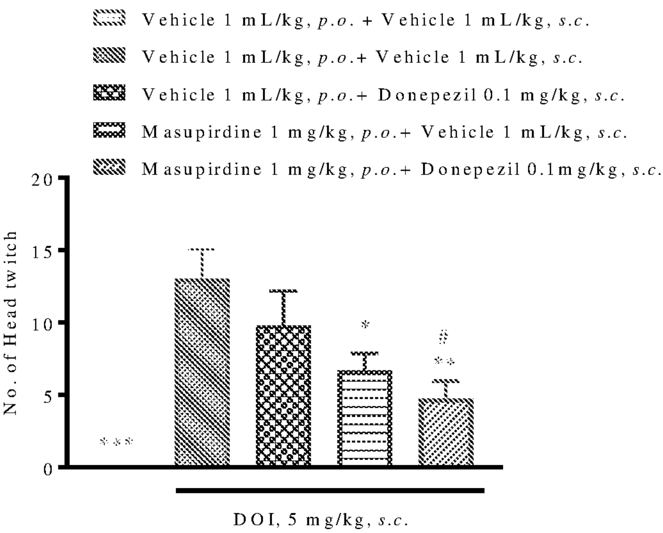

Data represents mean±SEM of head twitches.*P<0.001, P<0.01, *P<0.05 vs. DOI, One-way ANOVA followed by Dunnett's test (n=8-9). #P<0.05 vs. donepezil (Student's unpaired-t-test).

Figure 3: Effect of combined masupirdine and donepezil on hallucination compared to masupirdine or donepezil alone

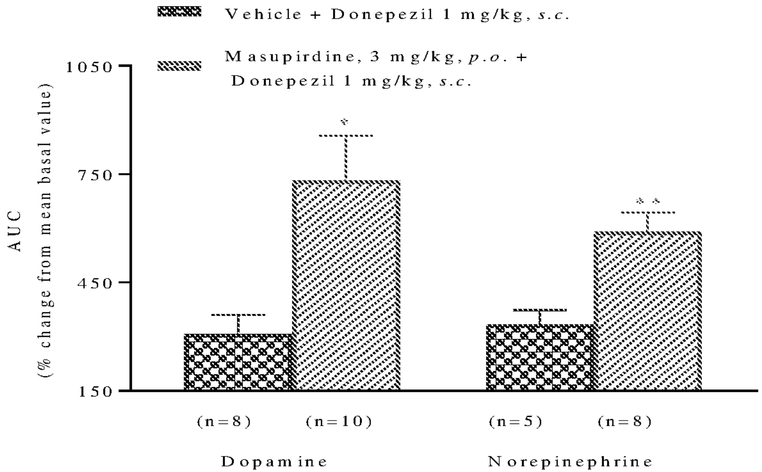

Data represents mean ± SEM. **P<0.01, *P<0.05 vs. donepezil alone (Student's unpaired-t-test).

Figure 4: Effect of combined masupirdine and donepezil on dopamine and norepinephrine levels compared to donepezil alone in prefrontal cortex of male Wistar rats.

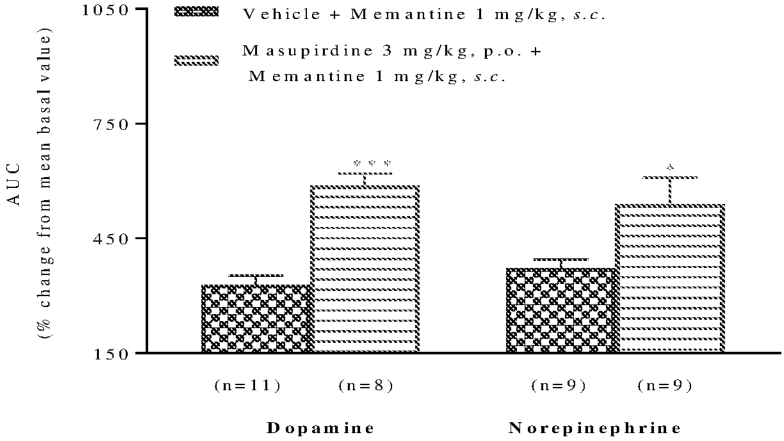
Data represents Mean ± SEM.***P<0.001, *P<0.05 vs. memantine alone (Unpaired-t-test).
Figure 5: Effect of combined masupirdine and memantine on dopamine and norepinephrine levels compared to memantine alone in prefrontal cortex of male Wistar rats.

METHODS FOR TREATING BEHAVIORAL AND PSYCHOLOGICAL SYMPTOMS IN PATIENTS WITH DEMENTIA

CROSS REFERENCE TO RELATED APPLICATIONS

This application is a national stage completion application of PCT Application No. PCT/IB2020/061367, filed Dec. 2, 2020, and claims priority from India application No. 201941049513, filed Dec. 2, 2019 and India application No. 201941049515, also filed Dec. 2, 2019. Each of these applications is incorporated by reference herein in its entirety.

FIELD OF THE INVENTION

The present invention provides a method for treating behavioral and psychological symptoms in patients with dementia comprising administering an effective dose of pure 5-$HT_6$ receptor antagonist and an acetylcholinesterase inhibitor or NMDA receptor antagonist. The present invention also relates to a pharmaceutical combination comprising pure 5-$HT_6$ receptor antagonist and an acetylcholinesterase inhibitor or NMDA receptor antagonist, in particular for treating behavioral and psychological symptoms in patients with dementia. The present invention further provides use of the said compounds in the manufacture of a medicament, and a pharmaceutical composition comprising the said compounds intended for the treatment of disorders described herein.

BACKGROUND OF THE INVENTION

Deterioration in thinking, memory, behavior, and the ability to perform activities of daily living falls under the broader domain of dementia. Alzheimer's disease (AD) dementia is the most common form of dementia. Other major forms include Lewy body dementia (LBD), vascular dementia (VD), Parkinson's disease (PD) dementia, dementia associated with schizophrenia, and frontotemporal dementia (FTD). Although they are pathologically different from each other, they have symptoms that are common and mixed forms often co-exist. Behavioral and psychological symptoms are one of the common symptoms observed across the forms of dementia which represent a heterogeneous group of non-cognitive symptoms and behaviors. Behavioral and psychological symptoms of dementia (BPSD) are also known as neuropsychiatric symptoms. BPSD constitutes a major component of the dementia syndrome irrespective of its subtype. It is estimated that BPSD affects up to 90% of all dementia subjects over the course of their illness, and is independently associated with poor outcomes, including distress among patients and caregivers, early and long-term institutionalization, misuse of medication, and increased health care costs. They are clinically as relevant as cognitive symptoms because they strongly correlate with the degree of functional and cognitive impairment. BPSD includes agitation/aggression, aberrant motor behavior, aberrant vocalizations, anxiety, elation, dysphoria, irritability, depression, apathy, disinhibition, delusions, hallucinations, and sleep or appetite changes. Clinical evidences suggest that there is a broad overlap between the behaviorally relevant circuits and networks associated with these symptoms. The Neuropsychiatric Inventory (NPI) scale is widely used to assess neuropsychological symptoms in patients with dementias.

Psychosis symptoms are common across dementia types with a prevalence of 20% to 70%. In addition to occurring in patients with AD, psychosis also occurs in patients with other dementias of a wide variety of etiologies (*J Cell Mol Med* 2012; 16:995-1012). Among patients with AD psychosis, it is reported that an increased occurrence of severe psychosis is associated with an increased presence of delusions and hallucinations as well as symptoms of agitation/aggression. Currently, no pharmacological treatment is approved for patients with AD psychosis, particularly, patients experiencing severe psychotic symptoms.

Agitation/aggression is highly prevalent in patients with dementia which involves emotional distress for patients and caregivers, risk of institutionalization, and faster rate of disease state progression. Individual items of agitation/aggression, aberrant motor behavior, aberrant vocalizations, irritability/lability, anxiety, and disinhibition from the NPI may represent agitation/aggression. Currently, no pharmacological treatment is approved for the treatment of agitation/aggression in patients with dementia. Apathy is also commonly observed in dementia and is a primary cause of caregiver distress. Apathy is characterized by lack of motivation, decreased initiative, akinesia, and emotional indifference. Currently, no pharmacological treatment is approved for the treatment of apathy in patients with dementia. Depression is also common in the dementia population. Although antidepressants are used for the management, evidence for utility is mixed. A high prevalence of sleep disorders is also observed in demented patients.

Combination of non-pharmacological and careful use of pharmacological interventions is the recommended therapeutic strategy for managing BPSD. Published literature indicates that modest symptomatic benefit is associated with short-term treatment of patients with BPSD using atypical antipsychotic agents like risperidone, olanzapine, and aripiprazole. However, benefits for longer-term treatment are less clear (*N Engl J Med.* 2006; 355(15):1525-1538). Moreover, the modest benefits must be balanced against significant safety concerns associated with these drugs, including risks of accelerated cognitive decline, stroke, and death, particularly with longer-term use. Atypical antipsychotics have been associated with statistically significant acceleration of cognitive deterioration in patients with AD. Pimavanserin, a 5-$HT_{2A}$ receptor antagonist which was recently approved for PD psychosis had shown statistically significant effect on Neuropsychiatric Inventory Nursing Home Version (NPI-NH) psychosis scale at week 6, however, no effect was for agitation in AD study (*The lancet neurology,* 2018, 17, 213-222; NCT02992132). Citalopram (30 mg daily dose) for agitation in AD study showed a significant decrease in agitation in 186 patients with AD (*JAMA* 2014; 311:682-91). Worsening of cognition and QT interval prolongation were seen in citalopram treatment group.

Given the modest efficacy of current therapies, there is an urgent need to identify novel pharmacological mechanisms through which one can address the current limitations like side effects, cognitive worsening while treating BPSD.

WO2015083179 discloses process for large scale production of 1-[(2-bromophenyl)sulfonyl]-5-methoxy-3-[(4-methyl-1-piperazinyl)methyl]-1h-indole dimesylate monohydrate.

WO2017199071 discloses a combination of pure 5-$HT_6$ receptor (5-$HT_6$R) antagonists and acetylcholinesterase inhibitors for the treatment of cognitive disorders.

WO2017199072 discloses a combination of pure 5-$HT_6$R antagonists and NMDA antagonist for the treatment of cognitive disorders.

WO2019008484 discloses the uses of a pure 5-$HT_6$R antagonist, specifically 1-[(2-Bromophenyl) sulfonyl]-5-methoxy-3-[(4-methyl-1-piperazinyl)methyl]-1H-indole or a pharmaceutically acceptable salt thereof. However, this patent application did not disclose the combination of 5-$HT_6$R antagonists and acetylcholinesterase inhibitors for the treatment of behavioral and psychological symptoms in patients with dementia.

The 5-$HT_6$R antagonists had shown the activity on one of the NPI domain that is apathy (WO2017/194496). There is no information on the potential utility on other important domains of NPI in this said patent WO2017/194496. The NPI domains though are clubbed under single scale but the causative biological reasons for each of these symptoms are different. A person skilled in the art would not expect that if a 5-$HT_6$ R antagonist is active in one domain, that means it will show activity in other domains as well. The effect of donepezil is mainly observed in the NPI domain namely apathy (*Int J Geriatr Psychiatry.* 2011 February; 26(2):150-7). Further, donepezil was evaluated for the treatment of agitation/aggression in patients with Alzheimer's disease, however, donepezil failed to show significant effect compared to placebo (*N Engl J Med.* 2007 Oct. 4; 357(14):1382-92).

The NMDA receptor antagonist, memantine is expected to work by blocking the glutamate in the brain (*Neurotox Res* (2013) 24:358-369) whereas the 5-$HT_6$R antagonists work by increasing the glutamate levels in the brain in addition to other mechanisms including increasing acetylcholine levels (*Expert Opin Investig Drugs.* 2015; 24(12): 1515-28). Thus given these contrasting mechanisms it is not anticipated that the combination of a pure 5-$HT_6$R antagonist and NMDA receptor antagonist would show coherence or positive effects in their pharmacological activity in the domains of BPSD.

Masupirdine (1-[(2-bromophenyl)sulfonyl]-5-methoxy-3-[(4-methyl-1-piperazinyl)methyl]-1H-indole) is a pure 5-$HT_6$R antagonist with high selectivity over closely related serotonin subtypes.

The instant invention provides pure 5-$HT_6$R antagonist or the pharmaceutically acceptable salt(s) thereof, which treats BPSD in combination with or as an adjunct to acetylcholinesterase inhibitors or NMDA receptor antagonist. The present invention is based on the unexpected and surprising finding that the combination of pure 5-$HT_6$R antagonist and the compounds which act as acetylcholinesterase inhibitor such as donepezil or NMDA receptor antagonist, memantine addresses in patients with dementia an array of behavioral and psychological symptoms like agitation/aggression, psychosis (delusions and/or hallucinations), anxiety, apathy and sleep disorders and others. Based on these results, one can infer that such combined administration and/or co-treatment of pure 5-$HT_6$R antagonist with acetylcholinesterase inhibitor or NMDA receptor antagonist, results in improved therapeutic efficacy in humans. Further, the pure 5-$HT_6$R antagonist, masupirdine or the pharmaceutically acceptable salt(s) thereof of the instant invention is more effective in combination with donepezil or memantine in the treatment of BPSD.

SUMMARY OF THE INVENTION

The present invention provides a method for the treatment of behavioral and psychological symptoms in patients with dementia, comprising administering an effective dose of a pure 5-$HT_6$ receptor antagonist and an acetylcholinesterase inhibitor or NMDA receptor antagonist.

In an aspect, the present invention provides a method for the treatment of behavioral and psychological symptoms in patients with Alzheimer's disease dementia, dementia associated with schizophrenia, Parkinson's disease dementia, Lewy body dementia, vascular dementia, and frontotemporal dementia, comprising administering an effective dose of pure 5-$HT_6$ receptor antagonist and an acetylcholinesterase inhibitor or NMDA receptor antagonist.

In another aspect, the present invention relates to a method for the treatment of behavioral and psychological symptoms in patients with dementia, comprising administering an effective dose of pure 5-$HT_6$ receptor antagonist and an acetylcholinesterase inhibitor or NMDA receptor antagonist, wherein the behavioral and psychological symptoms in dementia are selected from agitation/aggression, delusions and/or hallucinations, aberrant motor behavior, aberrant vocalizations, anxiety, elation/euphoria, irritability, depression/dysphoria, apathy, disinhibition, sleep and night time behavior, or appetite and eating change.

In another aspect, the present invention relates to a method for the treatment of behavioral and psychological symptoms in patients with dementia, comprising administering an effective dose of pure 5-$HT_6$ receptor antagonist and an acetylcholinesterase inhibitor or NMDA receptor antagonist, wherein the pure 5-$HT_6$ receptor antagonist is masupirdine or a pharmaceutically acceptable salt thereof.

In another aspect, the present invention relates to a method for the treatment of behavioral and psychological symptoms in patients with dementia, comprising administering an effective dose of masupirdine or a pharmaceutically acceptable salt thereof and an acetylcholinesterase inhibitor, wherein the acetylcholinesterase inhibitor is selected from donepezil, rivastigmine, and galantamine or a pharmaceutically acceptable salt thereof.

In another aspect, the present invention relates to a method for the treatment of behavioral and psychological symptoms in patients with dementia, comprising administering an effective dose of masupirdine or a pharmaceutically acceptable salt thereof and NMDA receptor antagonist, memantine or a pharmaceutically acceptable salt thereof.

In another aspect, the present invention relates to use of a pure 5-$HT_6$ receptor antagonist and an acetylcholinesterase inhibitor, in the manufacture of a medicament for the treatment of behavioral and psychological symptoms in patients with dementia, wherein the pure 5-$HT_6$ receptor antagonist is masupirdine or a pharmaceutically acceptable salt thereof.

In another aspect, the present invention relates to use of masupirdine or a pharmaceutically acceptable salt thereof and an acetylcholinesterase inhibitor, in the manufacture of a medicament for the treatment of behavioral and psychological symptoms in patients with dementia, wherein the acetylcholinesterase inhibitor is selected from donepezil, rivastigmine, and galantamine or a pharmaceutically acceptable salt thereof.

In another aspect, the present invention relates to use of masupirdine or a pharmaceutically acceptable salt thereof and NMDA receptor antagonist, memantine or a pharmaceutically acceptable salt thereof, in the manufacture of a medicament for the treatment of behavioral and psychological symptoms in patients with dementia.

In another aspect, the present invention relates to a pharmaceutical composition comprising pure 5-$HT_6$ receptor antagonist, masupirdine or a pharmaceutically acceptable salt thereof, and an acetylcholinesterase inhibitor for the treatment of behavioral and psychological symptoms in patients with dementia, wherein the acetylcholinesterase inhibitor is selected from donepezil, rivastigmine, and galantamine or a pharmaceutically acceptable salt thereof.

In another aspect, the present invention relates to a pharmaceutical composition comprising pure 5-$HT_6$ receptor antagonist, masupirdine or a pharmaceutically acceptable salt thereof, and NMDA receptor antagonist, memantine or a pharmaceutically acceptable salt thereof for the treatment of behavioral and psychological symptoms in patients with dementia.

In another aspect, the present invention relates to a pharmaceutical combination of pure 5-$HT_6$ receptor antagonist, masupirdine or a pharmaceutically acceptable salt thereof and an acetylcholinesterase inhibitor for the treatment of behavioral and psychological symptoms in patients with dementia, wherein the acetylcholinesterase inhibitor is selected from donepezil, rivastigmine, and galantamine or a pharmaceutically acceptable salt thereof.

In another aspect, the present invention relates to a pharmaceutical combination of pure 5-$HT_6$ receptor antagonist, masupirdine or a pharmaceutically acceptable salt thereof and NMDA receptor antagonist, memantine or a pharmaceutically acceptable salt thereof for the treatment of behavioral and psychological symptoms in patients with dementia.

BRIEF DESCRIPTION OF THE ACCOMPANYING DRAWINGS

FIG. 1: Effect of combined masupirdine and donepezil on aggression levels compared to masupirdine or donepezil alone.

FIG. 2: Effect of combined masupirdine and memantine on aggression levels compared to masupirdine or memantine alone.

FIG. 3: Effect of combined masupirdine and donepezil on hallucination compared to masupirdine or donepezil alone.

FIG. 4: Effect of combined masupirdine and donepezil on dopamine and norepinephrine levels compared to donepezil in prefrontal cortex of male Wistar rats.

FIG. 5: Effect of combined masupirdine and memantine combination on dopamine and norepinephrine levels compared to memantine in prefrontal cortex of male Wistar rats.

DETAILED DESCRIPTION OF THE INVENTION

Unless otherwise stated, the following terms used in the specifications and claims have the meanings as given below:

The term, "5-$HT_6$ receptor antagonist" as used herein refers to a ligand or drug that shows affinity towards 5-$HT_6$ receptor, blocks or inhibits the function/binding of 5-$HT_6$ receptor agonist.

The term, "pure 5-$HT_6$ receptor antagonist" as used herein refers to a 5-$HT_6$ receptor antagonist which has very high selectivity (>250 fold) over closely related serotonin subtypes like 5-$HT_{1A}$, 5-$HT_{1B}$, 5-$HT_{1D}$, 5-$HT_{2A}$, 5-$HT_{2C}$, 5-$HT_4$, 5-$HT_{5A}$, and 5-$HT_7$.

Example of pure 5-$HT_6$ receptor antagonist is (1-[(2-Bromophenyl)sulfonyl]-5-methoxy-3-[(4-methyl-1-piperazinyl)methyl]-1H-indole).

The international nonproprietary name (INN) for (1-[(2-Bromophenyl) sulfonyl]-5-methoxy-3-[(4-methyl-1-piperazinyl)methyl]-1H-indole) is masupirdine.

Example of pharmaceutically acceptable salt of above pure 5-$HT_6$ receptor antagonist, masupirdine is dimesylate monohydrate.

Masupirdine dimesylate monohydrate is also known as SUVN-502 which has the chemical structure as shown below.

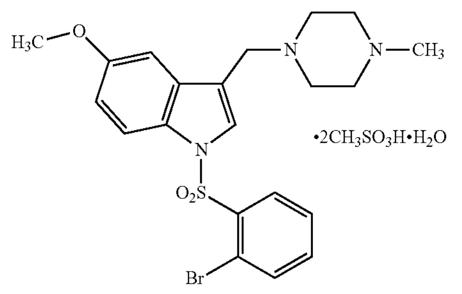

Masupirdine is commonly administered as masupirdine dimesylate monohydrate. The compound, masupirdine dimesylate monohydrate and its preparation were described in US patents U.S. Pat. Nos. 7,875,605, 9,540,321 and in article *J. Med. Chem.* 2017, 60, 5, 1843-1859.

The term, "active ingredient" or "active compound(s)" or "compound(s)" as used herein refers to a 5-$HT_6$ receptor antagonist or an acetylcholinesterase inhibitor or NMDA receptor antagonist. Preferably the 5-$HT_6$ receptor antagonist is (1-[(2-Bromophenyl)sulfonyl]-5-methoxy-3-[(4-methyl-1-piperazinyl)methyl]-1H-indole) or a pharmaceutically acceptable salt, the acetylcholinesterase inhibitor is donepezil, rivastigmine, galantamine or pharmaceutically acceptable salts thereof and NMDA receptor antagonist is memantine or pharmaceutically acceptable salts thereof.

The term, "acetylcholinesterase inhibitor" as used herein is a chemical or drug that inhibits acetylcholinesterase enzyme from breaking down acetylcholine, thereby increases levels of the neurotransmitter acetylcholine. Examples of acetyl cholinesterase inhibitors are; donepezil, rivastigmine, and galantamine. Preferably, the acetylcholinesterase inhibitor is donepezil, rivastigmine, galantamine, or pharmaceutically acceptable salts thereof.

Donepezil is a drug approved for the treatment of mild, moderate, and severe dementia of AD. Donepezil is a reversible inhibitor of the enzyme acetylcholinesterase and sold under trade name Aricept® as hydrochloride salt.

Rivastigmine is a drug approved for treatment of mild, moderate and severe dementia of AD. Rivastigmine is a reversible cholinesterase inhibitor and sold under trade name Exelon® and Exelon Patch® as tartrate salt.

Galantamine is a drug approved for treatment of mild, moderate and severe dementia of AD. Galantamine, a reversible, competitive acetylcholinesterase inhibitor and sold under trade name Razadyne® as hydrobromide salt.

The term, "NMDA receptor antagonist" as used herein refers to class of compounds which act on glutamatergic system by inhibiting the NMDA receptor. Example of NMDA receptor antagonist is memantine. Memantine is a drug approved for treatment of moderate to severe dementia of the AD. Memantine is sold under trade name Namenda® and Namenda XR® as hydrochloride salt.

The phrase, "an effective amount" or "an effective dose" is defined as an amount of a compound of the present invention that (i) treats the particular disease, condition, or disorder, (ii) eliminates one or more symptoms of the particular disease, condition or disorder and (iii) delays the onset of one or more symptoms of the particular disease, condition or disorder described herein.

The term, "pharmaceutically acceptable salt(s)" as used herein refers to salts of the active compound and are prepared by reaction with the appropriate organic or inorganic acids or acid derivatives, depending on the particular substituents found on the compounds described herein. The pharmaceutically acceptable salts include but are not limited to, dimesylate, dihydrochloride, oxalate, succinate, and tartrate and alike. Preferably, the pharmaceutically acceptable salts are dihydrochlorides and dimesylates. More preferably, the pharmaceutically acceptable salt is dimesylate or hydrochloride.

The term, "patient(s)" as used herein refers to an animal. Preferably the term "patient(s)" refers to a mammal. The term mammal includes animals such as mice, rats, dogs, rabbits, pigs, monkeys, elephants, camels, horses, and humans. More preferably the term "patient(s)" refers to humans.

The term "behavioral and psychological symptoms", also known as neuropsychiatric symptoms, refer to a heterogeneous group of non-cognitive symptoms and behaviors occurring in patients with dementia. BPSD constitute a major component of the dementia syndrome irrespective of its subtype. Behavioral and psychological symptoms include domains like agitation/aggression, delusions and/or hallucinations, aberrant motor behavior, aberrant vocalizations, anxiety, elation/euphoria, irritability, depression/dysphoria, apathy, disinhibition, sleep and night time behavior or appetite and eating change. It also refers to any physical or verbal behavior of dementia patients which has the effect of hurting or repelling others, and includes aggressive behaviors such as beating, kicking, biting, and screaming.

The term "dementia" as used herein includes Alzheimer's disease (AD) dementia, dementia associated with schizophrenia, Parkinson's disease (PD) dementia, Lewy body dementia (LBD), vascular dementia, and frontotemporal dementia (FTD).

The term "agitation/aggression" as used herein refers to "agitation and/or aggression".

The term "delusion and/or hallucinations" as used herein refers to "delusions or hallucinations, or delusions and hallucinations.

The term, "Alzheimer's disease" as used herein refers to dementia that causes problems with memory, thinking, and behavior. Alzheimer's disease can be mild, moderate or severe.

The term, "treatment" or "treating" as used herein refers to any treatment of a disease in a mammal, including: (a) slowing or arresting the development of clinical symptoms; and/or (b) causing the regression of clinical symptoms.

The term, "compound for use" as used herein embrace any one or more of the following: (1) use of a compound, (2) method of use of a compound, (3) use in the treatment of, (4) the use for the manufacture of pharmaceutical composition/medicament for treatment/treating or (5) method of treatment/treating/preventing/reducing/inhibiting comprising administering an effective amount of the active compound to a patient in need thereof.

EMBODIMENTS

The present invention encompasses all the examples described herein without limitation, however, preferred aspects and elements of the invention are discussed herein in the form of the following embodiments.

In one embodiment, the present invention relates to a method for the treatment of behavioral and psychological symptoms in patients with dementia comprising administering an effective dose of masupirdine or a pharmaceutically acceptable salt thereof and an acetylcholinesterase inhibitor.

In another embodiment, the present invention relates to a method for the treatment of behavioral and psychological symptoms in patients with dementia comprising administering an effective dose of masupirdine or a pharmaceutically acceptable salt thereof and NMDA receptor antagonist.

In embodiments, the dementia is selected from Alzheimer's disease dementia, dementia associated with schizophrenia, Parkinson's disease dementia, Lewy body dementia, vascular dementia, and frontotemporal dementia.

In embodiments, the behavioral and psychological symptoms in patient with dementia are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In another embodiment, the present invention relates to a method for the treatment of behavioral and psychological symptoms in patients with Alzheimer's disease dementia, comprising administering an effective dose of masupirdine or a pharmaceutically acceptable salt thereof and an acetylcholinesterase inhibitor.

In another embodiment, the present invention relates to a method for the treatment of behavioral and psychological symptoms in patients with dementia associated with schizophrenia, comprising administering an effective dose of masupirdine or a pharmaceutically acceptable salt thereof and an acetylcholinesterase inhibitor.

In another embodiment, the present invention relates to a method for the treatment of behavioral and psychological symptoms in patients with Parkinson's disease dementia, comprising administering an effective dose of masupirdine or a pharmaceutically acceptable salt thereof and an acetylcholinesterase inhibitor.

In another embodiment, the present invention relates to a method for the treatment of behavioral and psychological symptoms in patients with Lewy body dementia, comprising administering an effective dose of masupirdine or a pharmaceutically acceptable salt thereof and an acetylcholinesterase inhibitor.

In another embodiment, the present invention relates to a method for the treatment of behavioral and psychological symptoms in patients with vascular dementia, comprising administering an effective dose of masupirdine or a pharmaceutically acceptable salt thereof and an acetylcholinesterase inhibitor.

In another embodiment, the present invention relates to a method for the treatment of behavioral and psychological symptoms in patients with frontotemporal dementia, comprising administering an effective dose of masupirdine or a pharmaceutically acceptable salt thereof and an acetylcholinesterase inhibitor.

In another embodiment, the present invention relates to a method for the treatment of behavioral and psychological symptoms in patients with Alzheimer's disease dementia, comprising administering an effective dose of masupirdine or a pharmaceutically acceptable salt thereof and NMDA receptor antagonist.

In another embodiment, the present invention relates to a method for the treatment of behavioral and psychological symptoms in patients with dementia associated with schizophrenia, comprising administering an effective dose of masupirdine or a pharmaceutically acceptable salt thereof and NMDA receptor antagonist.

In another embodiment, the present invention relates to a method for the treatment of behavioral and psychological symptoms in patients with Parkinson's disease dementia, comprising administering an effective dose of masupirdine or a pharmaceutically acceptable salt thereof and NMDA receptor antagonist.

In another embodiment, the present invention relates to a method for the treatment of behavioral and psychological symptoms in patients with Lewy body dementia, comprising administering an effective dose of masupirdine or a pharmaceutically acceptable salt thereof and NMDA receptor antagonist.

In another embodiment, the present invention relates to a method for the treatment of behavioral and psychological symptoms in patients with vascular dementia, comprising administering an effective dose of masupirdine or a pharmaceutically acceptable salt thereof and NMDA receptor antagonist.

In another embodiment, the present invention relates to a method for the treatment of behavioral and psychological symptoms in patients with frontotemporal dementia, comprising administering an effective dose of masupirdine or a pharmaceutically acceptable salt thereof and NMDA receptor antagonist.

In embodiments, the behavioral and psychological symptoms in patient with Alzheimer's disease dementia are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In embodiments, the behavioral and psychological symptoms in patient with dementia associated with schizophrenia are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In embodiments, the behavioral and psychological symptoms in patient with Parkinson's disease dementia are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In embodiments, the behavioral and psychological symptoms in patient with Lewy body dementia are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In embodiments, the behavioral and psychological symptoms in patient with vascular dementia are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In embodiments, the behavioral and psychological symptoms in patient with frontotemporal dementia are selected from agitation/aggression, delusions and/or hallucinations, aberrant motor behavior, aberrant vocalizations, anxiety, elation/euphoria, irritability, depression/dysphoria, apathy, disinhibition, delusions, hallucinations, sleep and night-time behavior change, and appetite and eating change.

In embodiments, the acetylcholinesterase inhibitor is selected from donepezil, rivastigmine, and galantamine or a pharmaceutically acceptable salt thereof.

In embodiments, the NMDA receptor antagonist is memantine or a pharmaceutically acceptable salt thereof.

In another embodiment, the present invention relates to a method for the treatment of the behavioral and psychological symptom in patient with dementia comprising administering an effective dose of masupirdine or a pharmaceutically acceptable salt thereof and donepezil or a pharmaceutically acceptable salt thereof.

In another embodiment the present invention relates to a method for the treatment of the behavioral and psychological symptom in patient with dementia comprising administering an effective dose of masupirdine or a pharmaceutically acceptable salt thereof and memantine or a pharmaceutically acceptable salt thereof.

In some embodiments, the pharmaceutically acceptable salt of masupirdine is selected from mesylate, hydrochloride, oxalate, succinate, and tartrate salts.

In certain embodiments, the pharmaceutically acceptable salt of masupirdine is dimesylate monohydrate.

In embodiments, the pharmaceutically acceptable salt of donepezil is donepezil hydrochloride.

In embodiments, the pharmaceutically acceptable salt of memantine is memantine hydrochloride.

In preferred embodiment, the behavioral and psychological symptom in patient with dementia is agitation/aggression.

In preferred embodiment, the behavioral and psychological symptom in patient with dementia is delusions and/or hallucinations.

In preferred embodiment, the behavioral and psychological symptom in patient with dementia is delusions.

In preferred embodiment, the behavioral and psychological symptom in patient with dementia is hallucinations.

In preferred embodiment, the behavioral and psychological symptom in patient with dementia is sleep and night-time behavior change.

In preferred embodiment, the behavioral and psychological symptom in patient with dementia is appetite and eating change.

In preferred embodiment, the behavioral and psychological symptom in patient with dementia is aberrant motor behavior.

In preferred embodiment, the behavioral and psychological symptom in patient with dementia is aberrant vocalizations.

In preferred embodiment, the behavioral and psychological symptom in patient with dementia is irritability.

In preferred embodiment, the behavioral and psychological symptom in patient with dementia is apathy.

In preferred embodiment, the behavioral and psychological symptom in patient with dementia is depression/dysphoria.

In preferred embodiment, the behavioral and psychological symptom in patient with dementia is disinhibition.

In preferred embodiment, the behavioral and psychological symptom in patient with dementia is elation/euphoria.

In preferred embodiment, the behavioral and psychological symptom in patient with dementia is anxiety.

In preferred embodiment, the behavioral and psychological symptom in patient with Alzheimer's disease dementia is agitation/aggression.

In preferred embodiment, the behavioral and psychological symptom in patient with Alzheimer's disease dementia is delusions and/or hallucinations.

In preferred embodiment, the behavioral and psychological symptom in patient with Alzheimer's disease dementia is delusions.

In preferred embodiment, the behavioral and psychological symptom in patient with Alzheimer's disease dementia is hallucinations.

In preferred embodiment, the behavioral and psychological symptom in patient with Alzheimer's disease dementia is sleep and night-time behavior change.

In preferred embodiment, the behavioral and psychological symptom in patient with Alzheimer's disease dementia is appetite and eating change.

In preferred embodiment, the behavioral and psychological symptom in patient with Alzheimer's disease dementia is aberrant motor behavior.

In preferred embodiment, the behavioral and psychological symptom in patient with Alzheimer's disease dementia is aberrant vocalizations.

In preferred embodiment, the behavioral and psychological symptom in patient with Alzheimer's disease dementia is irritability.

In preferred embodiment, the behavioral and psychological symptom in patient with Alzheimer's disease dementia is apathy.

In preferred embodiment, the behavioral and psychological symptom in patient with Alzheimer's disease dementia is depression/dysphoria.

In preferred embodiment, the behavioral and psychological symptom in patient with Alzheimer's disease dementia is disinhibition.

In preferred embodiment, the behavioral and psychological symptom in patient with Alzheimer's disease dementia is elation/euphoria.

In preferred embodiment, the behavioral and psychological symptom in patient with Alzheimer's disease dementia is anxiety.

In another embodiment, the present invention relates to a method for the treatment of agitation/aggression in patients with Alzheimer's disease dementia, comprising administering an effective dose of masupirdine dimesylate monohydrate and donepezil hydrochloride or memantine hydrochloride.

In another embodiment, the present invention relates to a method for the treatment of delusions and/or hallucinations in patients with Alzheimer's disease dementia, comprising administering an effective dose of masupirdine dimesylate monohydrate and donepezil hydrochloride or memantine hydrochloride.

In another embodiment, the present invention relates to a method for the treatment of delusions in patients with Alzheimer's disease dementia, comprising administering an effective dose of masupirdine dimesylate monohydrate and donepezil hydrochloride or memantine hydrochloride.

In another embodiment, the present invention relates to a method for the treatment of hallucinations in patients with Alzheimer's disease dementia, comprising administering an effective dose of masupirdine dimesylate monohydrate and donepezil hydrochloride or memantine hydrochloride.

In another embodiment, the present invention relates to a method for the treatment of sleep and night-time behavior change in patients with Alzheimer's disease dementia, comprising administering an effective dose of masupirdine dimesylate monohydrate and donepezil hydrochloride or memantine hydrochloride.

In another embodiment, the present invention relates to a method for the treatment of appetite and eating change in patients with Alzheimer's disease dementia, comprising administering an effective dose of masupirdine dimesylate monohydrate and donepezil hydrochloride or memantine hydrochloride.

In another embodiment, the present invention relates to a method for the treatment of aberrant motor behavior in patients with Alzheimer's disease dementia, comprising administering an effective dose of masupirdine dimesylate monohydrate and donepezil hydrochloride or memantine hydrochloride.

In another embodiment, the present invention relates to a method for the treatment of aberrant vocalizations in patients with Alzheimer's disease dementia, comprising administering an effective dose of masupirdine dimesylate monohydrate and donepezil hydrochloride or memantine hydrochloride.

In another embodiment, the present invention relates to a method for the treatment of anxiety in patients with Alzheimer's disease dementia, comprising administering an effective dose of masupirdine dimesylate monohydrate and donepezil hydrochloride or memantine hydrochloride.

In another embodiment, the present invention relates to a method for the treatment of irritability in patients with Alzheimer's disease dementia, comprising administering an effective dose of masupirdine dimesylate monohydrate and donepezil hydrochloride or memantine hydrochloride.

In another embodiment, the present invention relates to a method for the treatment of apathy in patients with Alzheimer's disease dementia, comprising administering an effective dose of masupirdine dimesylate monohydrate and donepezil hydrochloride or memantine hydrochloride.

In another embodiment, the present invention relates to a method for the treatment of depression/dysphoria in patients with Alzheimer's disease dementia, comprising administering an effective dose of masupirdine dimesylate monohydrate and donepezil hydrochloride or memantine hydrochloride.

In another embodiment, the present invention relates to a method for the treatment of disinhibition in patients with Alzheimer's disease dementia, comprising administering an effective dose of masupirdine dimesylate monohydrate and donepezil hydrochloride or memantine hydrochloride.

In another embodiment, the present invention relates to a method for the treatment of elation/euphoria in patients with Alzheimer's disease dementia, comprising administering an effective dose of masupirdine dimesylate monohydrate and donepezil hydrochloride or memantine hydrochloride.

In another embodiment, the present invention relates to a method for the treatment of anxiety in patients with Alzheimer's disease dementia, comprising administering an effective dose of masupirdine dimesylate monohydrate and donepezil hydrochloride or memantine hydrochloride.

In another embodiment, the present invention relates to use of pure 5-$HT_6$ receptor antagonist, masupirdine or a pharmaceutically acceptable salt and an acetylcholinesterase inhibitor as described above in the manufacture of a medicament for the treatment of behavioral and psychological symptoms in patients with Alzheimer's disease dementia, dementia associated with schizophrenia, Parkinson's disease dementia, Lewy body dementia, vascular dementia, and frontotemporal dementia, wherein the behavioral and psychological symptoms are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In another embodiment, the present invention relates to use of pure 5-$HT_6$ receptor antagonist, masupirdine or a pharmaceutically acceptable salt and NMDA receptor antagonist as described above in the manufacture of a medicament for the treatment of behavioral and psychological symptoms in patients with Alzheimer's disease dementia, dementia associated with schizophrenia, Parkinson's disease dementia, Lewy body dementia, vascular dementia, and frontotemporal dementia, wherein the behavioral and psychological symptoms are selected from agitation/aggression, delusions and/or hallucinations, aberrant motor behavior, aberrant vocalizations, anxiety, elation/euphoria, irritability, depression/dysphoria, apathy, disinhibition, delusions, hallucinations, sleep and night-time behavior change, and appetite and eating change.

In embodiments of the present invention, the pure 5-$HT_6$ receptor antagonist and acetylcholinesterase inhibitor or NMDA receptor antagonist as described above can be administered to the patient simultaneously, separately, or sequentially.

In embodiments of the present invention, the pure 5-$HT_6$ receptor antagonist as described above can be administered to the patient in combination with or as an adjunct to acetylcholinesterase inhibitor or NMDA receptor antagonist.

In another embodiment, the present invention relates to a pharmaceutical combination of pure 5-$HT_6$ receptor antagonist and an acetylcholinesterase inhibitor; wherein the pure 5-$HT_6$ receptor antagonist is masupirdine or a pharmaceutically acceptable salt thereof and acetylcholinesterase inhibitor is donepezil, rivastigmine, and galantamine, or a pharmaceutically acceptable salt thereof.

In another embodiment, the present invention relates to a pharmaceutical combination of pure 5-$HT_6$ receptor antagonist and NMDA receptor antagonist; wherein the pure 5-$HT_6$ receptor antagonist is masupirdine or a pharmaceutically acceptable salt thereof and NMDA receptor antagonist is memantine or a pharmaceutically acceptable salt thereof.

In another aspect, the present invention relates to a pharmaceutical combination comprising masupirdine dimesylate monohydrate and donepezil hydrochloride.

In another aspect, the present invention relates to a pharmaceutical combination comprising masupirdine dimesylate monohydrate and memantine hydrochloride.

In another embodiment, the present invention relates to the said pharmaceutical combination for the treatment of behavioral and psychological symptoms in patients with Alzheimer's disease dementia, dementia associated with schizophrenia, Parkinson's disease dementia, Lewy body dementia, vascular dementia, and frontotemporal dementia, wherein the behavioral and psychological symptoms are selected from agitation/aggression, delusions and/or hallucinations, aberrant motor behavior, aberrant vocalizations, anxiety, elation/euphoria, irritability, depression/dysphoria, apathy, disinhibition, sleep and night-time behavior change, and appetite and eating change.

In another embodiment, the present invention relates to the said pharmaceutical combination for the treatment of agitation/aggression in patients with Alzheimer's disease dementia.

In another embodiment, the present invention relates to the said pharmaceutical combination for the treatment of delusions and/or hallucinations in patients with Alzheimer's disease dementia.

In yet another aspect, the active ingredients of the present invention can be administered in all possible routes of administration.

In yet another aspect, the active ingredients of the present invention may be administered by oral, nasal, local, or parenteral routes.

In yet another aspect, the active ingredients of the present invention can be administered by the same or different route of administration. For instance, the 5-$HT_6$ receptor antagonist of the instant invention can be administered orally and the acetylcholinesterase inhibitor or NMDA receptor antagonist can be administered transdermally.

In yet another aspect, the active ingredients of the present invention are normally administered by formulating the active ingredients into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, co-solvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pre-gelatinized starch, sodium starch glycolate, corn starch or derivatives thereof, povidone, crospovidone, calcium stearate, glyceryl monostearate, glyceryl palmitostearate, talc, colloidal silicon dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active ingredients of the invention may be formulated in the form of pills, tablets, coated tablets, capsules, powder, granules, pellets, patches, implants, films, semi-solids, liquids, gels, aerosols, emulsions, elixirs and the like. Such pharmaceutical compositions and processes for preparing same are well known in the art.

In yet another aspect, the pharmaceutical composition of the present invention contains 1 to 90%, 5 to 75% and 10 to 60% by weight of the active compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

In yet another aspect, the pharmaceutical composition of the present invention can be conventional formulations such as immediate release formulations, modified release formulations such as sustained release formulations, delayed release formulations, and extended release formulations or new delivery systems such as orally disintegrating formulations and transdermal patches.

The dose of the active compounds can vary depending on factors such as age and weight of patient, nature, route of administration and severity of the disease to be treated and such other factors.

In yet another aspect, the 5-$HT_6$ receptor antagonist, masupirdine or a pharmaceutically acceptable salt thereof can be administered with acetylcholinesterase inhibitor or NMDA receptor antagonist at a daily dose of 25 mg to 125 mg; such as 25, 30, 50, 75, 100, or 125, preferably at a daily dose of 25, 30, 50, 75, 100 or 125 mg and most preferably at a daily dose of 10, 25, 50, 75, 100 or 125 mg.

In yet another aspect, the acetylcholinesterase inhibitor can be co-administered with 5-$HT_6$ receptor antagonist at a daily dose of 5 mg to 30 mg; 5, 6, 8, 9.5, 10, 12, 13, 13.3, 15, 16, 23, 24, 25 or 30 mg, preferably at a daily dose of 5, 6, 8, 9.5, 10, 12, 13, 13.3, 16, 23, 24, or 25 mg and most preferably at a daily dose of 5, 6, 8, 9.5, 10, 12, 13.3, 16, 23 or 24 mg.

In yet another aspect, the acetylcholinesterase inhibitor, donepezil can be co-administered with 5-$HT_6$ receptor antagonist at a daily dose of 5 mg to 30 mg; such as 5, 10, 15, 23, 25 or 30 mg, preferably at a daily dose of 5, 10, 23 or 25 mg and most preferably at a daily dose of 5, 10 or 23 mg.

In yet another aspect, the NMDA receptor antagonist, memantine can be co-administered with 5-$HT_6$ receptor antagonist at a daily dose of 5 mg to 40 mg; such as 5, 7, 10, 14, 20, 21, 28 or 40 mg, preferably at a daily dose of 5, 7, 10, 14, 21 or 28 mg.

In yet another aspect, the treatment comprises administering to the patient 25 mg to 125 mg of masupirdine or a pharmaceutically acceptable salt thereof, per day.

In yet another aspect, the treatment comprises administering to the patient 50 mg to 100 mg of masupirdine or a pharmaceutically acceptable salt thereof, per day.

In yet another aspect, the treatment comprises administering to the patient 25 mg to 50 mg of masupirdine or a pharmaceutically acceptable salt thereof, per day.

In yet another aspect, the treatment comprises administering to the patient 75 mg to 100 mg of masupirdine or a pharmaceutically acceptable salt thereof, per day.

In yet another aspect, the treatment comprises administering to the patient 25 mg to 75 mg of masupirdine or a pharmaceutically acceptable salt thereof, per day.

In yet another aspect, the treatment comprises administering to the patient 75 mg to 125 mg of masupirdine or a pharmaceutically acceptable salt thereof, per day.

In yet another aspect, the treatment comprises administering to the patient 5 mg to 25 mg of donepezil or a pharmaceutically acceptable salt thereof, per day.

In yet another aspect, the treatment comprises administering to the patient 5 mg, 10 mg or 23 mg of donepezil or a pharmaceutically acceptable salt thereof, per day.

In yet another aspect, the treatment comprises administering to the patient 5 mg to 30 mg of memantine or a pharmaceutically acceptable salt thereof, per day.

In yet another aspect, the treatment comprises administering to the patient 5 mg to 25 mg of memantine or a pharmaceutically acceptable salt thereof, per day.

In yet another aspect, the treatment comprises administering to the patient 5 mg, 7 mg, 14 mg, 10 mg, 21 mg, 25 mg, 28 mg or 30 mg of memantine or a pharmaceutically acceptable salt thereof, per day.

In yet another aspect, the treatment comprises administering the 5-$HT_6$ receptor antagonist, masupirdine or a pharmaceutically acceptable salt thereof and acetylcholinesterase inhibitor or NMDA receptor antagonist, to the patient one to three times per day, one to three times per week or one to three times per month. Preferably, the treatment comprises administering the compound to a patient once a day, twice a day or thrice a day. More preferably, the treatment comprises administering the compound to a patient once a day or twice a day.

EXAMPLES

Abbreviations

5-$HT_{1A}$: 5-Hydroxytryptamine 1A receptor
5-$HT_{1B}$: 5-Hydroxytryptamine 1B receptor
5-$HT_{1D}$: 5-Hydroxytryptamine 1D receptor
5-$HT_{2A}$: 5-Hydroxytryptamine 2A receptor
5-$HT_{2C}$: 5-Hydroxytryptamine 2C receptor
5-$HT_4$: 5-Hydroxytryptamine 4 receptor
5-$HT_{5A}$: 5-Hydroxytryptamine 5A receptor
5-$HT_6$: 5-Hydroxytryptamine 6 receptor
5-$HT_7$: 5-Hydroxytryptamine 7 receptor
cAMP: Cyclic adenosine monophosphate
$CaCl_2$: Calcium chloride
DOI: 2,5-Dimethoxy-4-iodoamphetamine
$EC_{50}$: Half maximal effective concentration
EDTA: Ethylenediaminetetraacetic acid
GPCR: G-Protein Coupled Receptor
g: Grams
HCl: Hydrochloric acid
h: Hour(s)
i.p: Intraperitoneal
$K_b$: Binding constant
$K_i$: Inhibitory constant
kg: Kilogram
KCl: Potassium chloride
LC-MS/MS: Liquid chromatography/Tandem mass spectrometry
$MgCl_2$: Magnesium chloride
mg: Milligram
min: Minutes
$MgCl_2$: Magnesium chloride
nM: Nanomolar
p.o.: Per oral
μM: Micromolar
μL: Microliter
mmol or mM: Millimolar
NaCl: Sodium chloride
s.c.: Subcutaneous

Example 1

Determination of $K_b$ Values at 5-$HT_6$ Receptor

A stable CHO cell line expressing recombinant human 5-$HT_6$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compound or standard agonist, cells were serum starved overnight. Increasing concentrations of test compound were added along with 10 μM of serotonin in OptiMEM medium to the cells. The incubation was continued at 37° C. in $CO_2$ incubator for 4 h. Medium was removed and cells were washed with phosphate buffered saline. The cells were lysed and luciferase activity was measured in a Lumino meter. Luminescence was plotted against the compound concentrations using GraphPad Prism software. $EC_{50}$ value of the compound was defined as the concentration required in reducing the luciferase activity by 50%. The $K_b$ value was calculated by feeding the concentration of agonist used in the assay and its $EC_{50}$ value in the same software.

References: *Molecular Brain Research,* 2001, 90, 110-117 and *British Journal of Pharmacology,* 2006, 148, 1133-1143.

Masupirdine exhibits antagonistic activity in CRE-Luc based reporter gene assay on the human recombinant 5-$HT_6$ receptor with no detectable agonist activity. The $K_b$ value of masupirdine is 4.2±0.9 nM.

Example 2

Determination of $K_i$ Value at 5-$HT_6$ Receptor

Compound was tested at MDS pharma services and Novascreen according to the following procedures.

Materials and Methods

Receptor source: Human recombinant 5-$HT_6$ receptor expressed in HeLa cells
Radioligand: [$^3$H]-LSD (60-80 Ci/mmol)
Final ligand concentration—[1.5 nM]
Non-Specific Ligand: 5 μM Serotonin (5-HT)
Reference compound: Methiothepin mesylate
Positive control: Methiothepin mesylate
Incubation conditions: Reactions were carried out in 50 mM Tris-HCl (pH 7.4) containing 10 mM $MgCl_2$, 0.5 mM EDTA for 60 min at 37° C. The reaction was terminated by rapid vacuum filtration onto the glass fiber filters. Radioactivity trapped onto the filters was determined and compared to the control values in order to ascertain any interactions of the test compound with the cloned serotonin 5-$HT_6$ binding site.

Reference: *Molecular Pharmacology,* 1993, 43, 320-327.

Masupirdine selectively binds to 5-$HT_6$ receptor when tested by the in-vitro radioligand binding technique on the human recombinant 5-$HT_6$ receptor. The $K_i$ value of masupirdine is 2.04 nM.

Example 3

Determination of $K_i$ Value at 5-$HT_{2A}$ Receptor

Compound was tested according to the following procedures.

Materials and Methods

Receptor source: Recombinant mammalian cells
Radioligand: [$^3$H]-Ketanserine (47.3 Ci/mmol)
Final ligand concentration—[1.75 nM]
Non-Specific Ligand: 0.1 mM 1-Naphthylpiperazine (1-NP)
Reference compound: 1-Naphthylpiperazine (1-NP)
Positive control: 1-Naphthylpiperazine (1-NP)
Incubation conditions: Reactions were carried out in 67 mM Tris-HCl (pH 7.4) for 1 h at 37° C. The reaction was terminated by rapid vacuum filtration onto the glass fiber filters. Radioactivity trapped onto the filters was determined and compared to the control values in order to ascertain any interactions of the test compound with the cloned serotonin 5-$HT_{2A}$ binding site.
Reference: *Methods in Molecular Biology,* 2002, 190, 31-49

Masupirdine binds weakly to 5-$HT_{2A}$ receptors when tested by the in-vitro radioligand binding technique on the human recombinant 5-$HT_{2A}$ receptor. The $K_i$ value of masupirdine is 2514±377 nM.

Example 4

Masupirdine was also evaluated for its 5-$HT_6$ receptor selectivity over closely related serotonin subtypes like 5-$HT_{1A}$, 5-$HT_{1B}$, 5-$HT_{1D}$, 5-$HT_{2A}$, 5-$HT_{2C}$, 5-$HT_4$, 5-$HT_{5A}$, and 5-$HT_7$ in commercial panel at Novascreen.

Masupirdine has shown selectivity of more than 250-fold, over these receptor subtypes.

Example 5: Resident-Intruder Task

Experimental Procedure:

Male Swiss albino mice of weight range 30-40 g (Resident) and 15-25 g (Intruder) were used. Resident mice were habituated individually with an ovariectomized female mouse in each cage for at least 2 weeks and intruders were habituated socially for at least 5 days. β-Estradiol at a dose of 0.2 mg/kg, s.c. was administered to ovariectomized female mice during habituation. After habituation for 3 weeks, the intruder was exposed to resident mice for a period of 10 min in the home cage of resident animal and duration of attack was recorded for two days (day 1 & 2). During this 10 min exposure period, ovariectomized female mice were removed from resident cage, resident animals were randomized based on their duration of attack. On day 4 (from initial exposure), resident animals were administered respective treatments. Masupirdine (0.30 mg/kg, p.o.) was administered 60 min prior to the trial and donepezil (0.30 mg/kg, i.p.) or memantine (0.30 mg/kg, i.p.) was administered 30 min prior to the trial. After post dose interval resident mice were exposed to same intruder for 10 min and duration of attack was recorded. Data were analyzed using GraphPad Prism software.

Observations:

Vehicle treated group showed equal duration of attack when compared with its basal. Group treated with masupirdine (0.30 mg/kg, p.o.) alone showed equal duration of attack when compared with its basal. Group treated with donepezil (0.30 mg/kg, i.p.) or memantine (0.30 mg/kg, i.p.) alone showed decrease in duration of attack when compared with its basal; however it was not statistically significant. Group treated with the combination of masupirdine and donepezil or memantine showed significant decrease in duration of attack when compared with its basal ($p<0.01$), demonstrating synergistic effect when administered as combination (FIG. 1 and FIG. 2).

Conclusion:

Combined anti-aggressive like activity of masupirdine and donepezil or memantine was better than either alone treatment in resident-intruder task in Swiss albino mice.

Example 6: Head Twitch Response

Experimental Procedure:

DOI induced head twitch response is considered to be a behavioral model of hallucination (Pharmacol Rep. 2012; 64(6):1567-72). Male Wistar rats of 200-290 g were weighed and randomized according to their body weights. On day 1, rats were first habituated to the arena for 15 min. On day 2, masupirdine was administered 1 h before trial. Donepezil was administered 30 min before the trial. 15 min before the trial, rats were subjected to habituation and immediately following the habituation, DOI, 5 mg/kg s.c was administered. The rats were then placed in the arena and head twitches were recorded for 10 min. Data were analyzed using GraphPad Prism software.

Observations:

Rats treated with DOI (5 mg/kg, s.c.) showed an increase in head twitches in comparison to the vehicle treated rats. Masupirdine significantly reduced the number of head twitches at a dose of 1 mg/kg, p.o. Masupirdine in combination with donepezil significantly reduced the number of head twitches in comparison to the standard of care (donepezil) (FIG. 3).

Conclusion: Masupirdine in combination with donepezil can attenuate visual hallucinations.

Example 7: Modulation of Norepinephrine and Dopamine Levels in Cortex

Experimental Procedure

Male Wistar rats (240-300 g body weight) were stereotaxically implanted with a microdialysis guide cannula in prefrontal cortex (PFC; AP: +3.2 mm, ML: −0.5 mm, DV: −1.0 mm) under isoflurane anesthesia. Co-ordinates were taken according to atlas for the rat brain (Paxinos and Watson 2004) with reference points taken from bregma and vertical from the skull. The rats were allowed to recover individually for four days in a round bottom Plexiglas bowl with free access to feed and water.

Sixteen hours before start of the study, a pre-equilibrated microdialysis probe (4 mm dialysis membrane) was inserted into PFC through the guide cannula. On the day of study, probe was perfused with artificial cerebrospinal fluid (aCSF; NaCl 150 mmol, KCl 3.0 mmol, $MgCl_2$ 0.9 mmol, $CaCl_2.2H_2O$ 1.7 mmol, pH 6.2) at a flow rate of 1.5 μL/min and a stabilization period of 2 h was maintained. Four basal samples were collected at 30 min intervals prior to the treatment of masupirdine (3 mg/kg, p.o.) or vehicle. Donepezil (1 mg/kg, s.c.) or memantine (1 mg/kg, s.c.) or vehicle was administered 30 min after administration of masupirdine. Dialysate samples were collected for an additional period of 4 h post treatment of masupirdine (3 mg/kg, p.o.). Dialysates were stored below −50° C. prior to analysis.

Norepinephrine and dopamine levels in dialysates were quantified using LC-MS/MS method.

Area under the curve (AUC) values for percent change in neurotransmitter levels were calculated and the statistical significance between the mean AUC value after combination treatment was compared against donepezil treatment using students unpaired t-test. Statistical significance was considered at a p value less than 0.05.

Observations:

Treatment with donepezil (1 mg/kg, s.c.) produced increase in cortical norepinephrine levels with AUC value of 333.77±39.77, whereas combination of masupirdine (3 mg/kg, p.o) and donepezil (1 mg/kg, s.c.) produced significantly higher AUC (590.6±53.01) compared to donepezil alone. These results indicate that the combination produced about 77% higher increase in cortical norepinephrine levels (FIG. 4).

Similarly, treatment with donepezil (1 mg/kg, s.c.) produced increase in cortical dopamine levels with AUC value of 307.79±52.22, whereas combination of masupirdine (3 mg/kg, p.o.) and donepezil (1 mg/kg, s.c.) produced significantly higher AUC (732.12±124.42) compared to donepezil alone. Results from this study indicate that the combination produced about 138% higher increase in cortical dopamine levels (FIG. 4).

Treatment with memantine (1 mg/kg, s.c.) produced increase in cortical norepinephrine levels with AUC value of 371.34±22.45, whereas combination of masupirdine (3 mg/kg, p.o.) and memantine (1 mg/kg, s.c.) produced significantly higher AUC values (539.31±69.12) compared to memantine alone. These results indicate that combination produced about 45% higher increase in cortical norepinephrine levels (FIG. 5).

Similarly, treatment with memantine (1 mg/kg, s.c.) produced increase in cortical dopamine levels with AUC value of 327.75±24.99, whereas combination of masupirdine (3 mg/kg, p.o.) and memantine (1 mg/kg, s.c.) produced significantly higher AUC values (587.31±32.47) compared to memantine alone. Results from this study indicate that combination produced about 79% higher increase in cortical dopamine levels (FIG. 5).

Conclusion: Norepinephrine and dopamine levels in the cortex play an important role in the management of neuropsychiatric disorders. Masupirdine potentiates the effects of donepezil or memantine on cortical levels of these neurotransmitters indicating that the combination of masupirdine with donepezil or memantine may have potential in the treatment of behavioral and psychiatric disorders.

We claim:

1. A method for the treatment of agitation/aggression in a patient with dementia comprising the step of administering an effective dose of masupirdine, or a pharmaceutically acceptable salt thereof, and an acetylcholinesterase inhibitor or NMDA receptor antagonist, wherein the acetylcholinesterase inhibitor is donepezil or a pharmaceutically acceptable salt thereof;

and the NMDA receptor antagonist is memantine or a pharmaceutically acceptable salt thereof.

2. The method of claim 1, wherein the pharmaceutically acceptable salt of masupirdine is dimesylate monohydrate.

3. The method of claim 1, wherein the acetylcholinesterase inhibitor is donepezil hydrochloride.

4. The method of claim 1, wherein the NMDA receptor antagonist is memantine hydrochloride.

5. The method for the treatment as claimed in claim 1, wherein the treatment comprises administering an effective dose of masupirdine dimesylate monohydrate and donepezil hydrochloride.

6. The method for the treatment as claimed in claim 1, wherein the treatment comprises administering an effective dose of masupirdine dimesylate monohydrate and memantine hydrochloride.

7. The method of claim 1, wherein the dementia is selected from Alzheimer's disease dementia, dementia associated with schizophrenia, Parkinson's disease dementia, Lewy body dementia, vascular dementia, or frontotemporal dementia.

8. The method of claim 1, wherein the agitation/aggression, is in a patient with Alzheimer's disease dementia.

9. The method of claim 1, wherein the agitation/aggression is in a patient with Parkinson's disease dementia.

10. The method of claim 1, wherein the treatment comprises administering to the patient 25 mg to 125 mg of masupirdine or a pharmaceutically acceptable salt thereof, per day.

11. The method of claim 1, wherein the treatment comprises administering to the patient 25 mg to 75 mg of masupirdine or a pharmaceutically acceptable salt thereof, per day.

12. The method of claim 1, wherein the treatment comprises administering to the patient 75 mg to 125 mg of masupirdine or a pharmaceutically acceptable salt thereof, per day.

13. The method of claim 1, wherein the treatment comprises administering to the patient 50 mg or 100 mg of masupirdine or a pharmaceutically acceptable salt thereof, per day.

14. The method of claim 1, wherein the treatment comprises administering to the patient 5 mg to 25 mg of donepezil or a pharmaceutically acceptable salt thereof, per day.

15. The method of claim 1, wherein the treatment comprises administering to the patient 5 mg to 30 mg of memantine or a pharmaceutically acceptable salt thereof, per day.

16. The method as claimed in claim 5, wherein the dementia is selected from Alzheimer's disease dementia, dementia associated with schizophrenia, Parkinson's disease dementia, Lewy body dementia, vascular dementia, and frontotemporal dementia.

17. The method as claimed in claim 6, wherein the dementia is selected from Alzheimer's disease dementia, dementia associated with schizophrenia, Parkinson's disease dementia, Lewy body dementia, vascular dementia, and frontotemporal dementia.

* * * * *